United States Patent [19]

Freundlich et al.

[11] Patent Number: 5,069,667
[45] Date of Patent: Dec. 3, 1991

[54] DEVICE FOR EFFECTING SAFE REMOVAL OF A USED NEEDLE

[76] Inventors: Lawrence F. Freundlich, 923 N. First St., New Hyde Park, N.Y. 11040; Arthur Karmen, 110 Colonial Pkwy., Manhasset, N.Y. 11030

[21] Appl. No.: 556,964

[22] Filed: Jul. 24, 1990

[51] Int. Cl.⁵ ............................................. A61M 5/00
[52] U.S. Cl. ...................................... 604/110; 206/366
[58] Field of Search ............... 604/110, 192, 198, 263; 128/763; 206/365, 366, 63.5

[56] References Cited

U.S. PATENT DOCUMENTS

| | | | |
|---|---|---|---|
| 4,375,849 | 3/1983 | Hanifi | 206/366 |
| 4,576,281 | 3/1986 | Kirksey | 206/370 |
| 4,738,362 | 4/1988 | Burns et al. | 206/366 |
| 4,862,573 | 9/1989 | Kelson et al. | 206/366 X |
| 4,867,309 | 9/1989 | Germain | 206/366 |
| 4,922,597 | 5/1990 | Ikeda et al. | 206/366 X |
| 4,986,811 | 1/1991 | Thead et al. | 604/110 |
| 4,986,816 | 1/1991 | Steiner et al. | 604/192 |

FOREIGN PATENT DOCUMENTS 2199497  7/1988  United Kingdom ............... 604/192
2205043 11/1988  United Kingdom ............... 604/192

Primary Examiner—Max Hindenburg
Attorney, Agent, or Firm—Nicholas J. Garofalo

[57] ABSTRACT

A device for protecting the user of a medical blood drawing instrument of the evacuated tube type from being pricked by the needle when removing it from the instrument. An end portion of the needle is threadly engaged in the instrument; a splined portion of the needle is disposed externally of the instrument; and the splined portion is normally engaged by a sheath protectively covering the needle before use is made of the needle. After removal of the sheath, use is made of the needle in a venipuncturing action. When the used needle is to be separated from the instrument, the needle with its splined portion is inserted into a passage of an upper member of the device. A cam mounted in the upper member is subject to being actuated by the user to engage the splined portion and hold the needle fast, so that the instrument may be turned relative to and unthreaded from the needle. The hold of the cam upon the needle is then manually released by the user, whereupon its release the separated needle will drop out of the passage into a disposable container below.

5 Claims, 1 Drawing Sheet

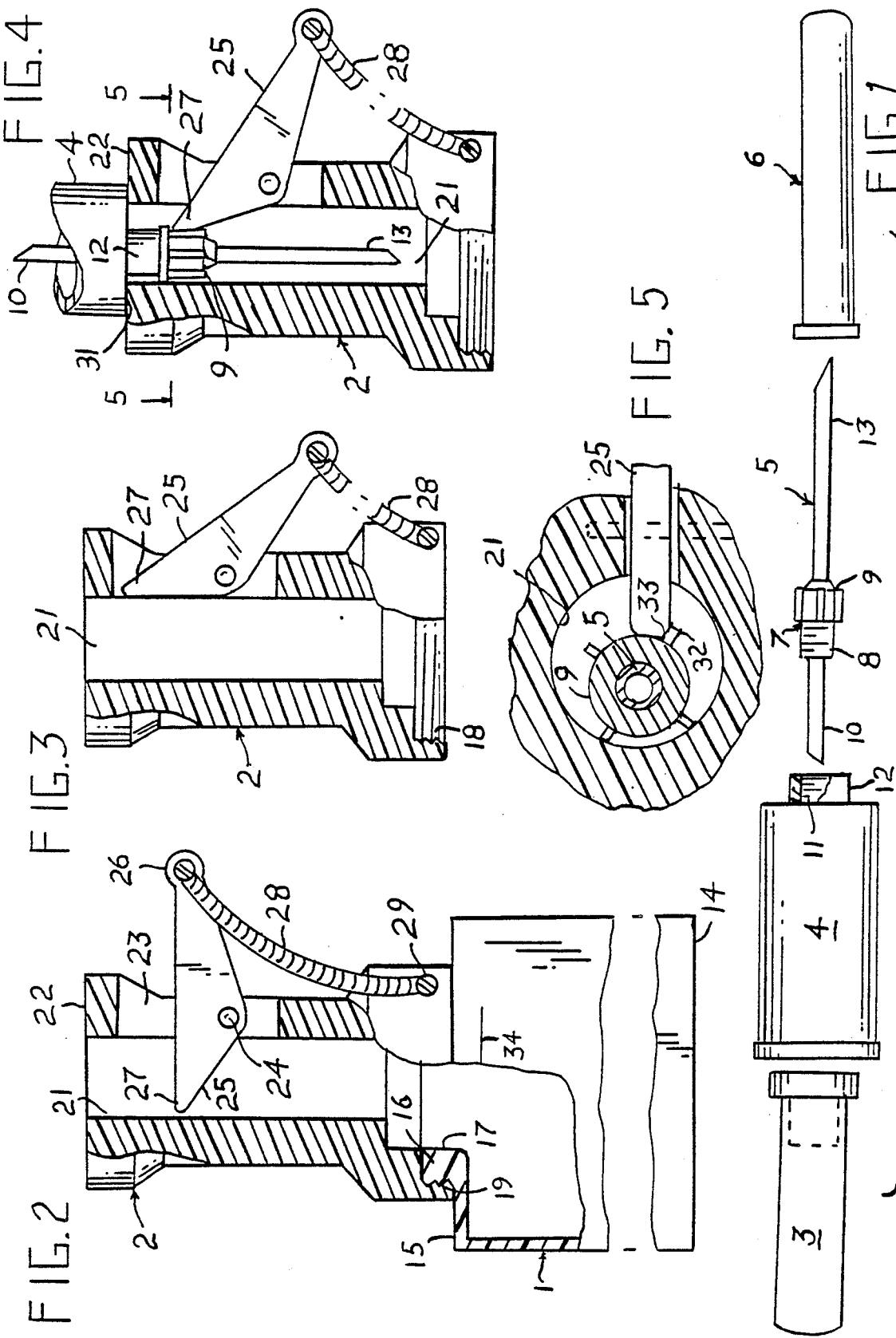

DEVICE FOR EFFECTING SAFE REMOVAL OF A USED NEEDLE

BACKGROUND OF THE INVENTION

This invention is directed to a device for protecting the user, commonly the phlebotomist, from becoming pricked by the needle when removing it from a blood drawing instrument, which needle might have become contaminated in a venipuncturing process. A device of this general nature is known from our co-pending application, Ser. No. 07/512,466, filed Apr. 23, 1990. The present invention, however, varies from the subject of our co-pending application in that it is directed primarily to camming means of a nature for holding the needle fast against relative movement after it has been unsheathed, so as to enable the instrument to be unthreaded from the needle.

Generally, a syringe or an evacuated tube type instrument is employed in venipuncturing to obtain blood test samples. Many phlebotomists prefer to use the evacuated tube type instrument for this purpose. This instrument includes a barrel that is open at both ends. A double ended needle is adapted to be engaged in a front end of the barrel in a manner in which one end of the needle extends into the barrel and the other end projects from the barrel. The needle has a hub intermediately of its ends. A rear portion of the hub is threaded and is adapted to be engaged with complementary threads in the barrel. And a forward portion of the hub has straight splines with which complimentary splines of a protective sheath disposed over the external portion of the needle are slidably engaged. And the barrel has an open rear end into which a rubber stoppered evacuated tube is adapted in use of the instrument to be slidably entered to be punctured by the portion of the needle within the barrel.

In making use of the evacuated tube type instrument, it is customary for the phlebotomist to remove the sheath from the needle by hand. He does this by holding the barrel in one hand and pulling the sheath from the needle with the other hand. At this time the unused needle is sterile. Accordingly, the phlebotomist is normally safe from becoming infected if he should become accidentally pricked by the needle when removing the sheath.

But, after the instrument has been used for blood drawing, the needle may have become contaminated. It is then that the phlebotomist must be extra careful in removing the used needle from the instrument to avoid being pricked and possibly infected. With this danger being ever present, the device embodying the present invention has been designed to enable the phlebotomist to safely effect removal of the needle by means of the device and not by hand.

Accordingly, a general object of this invention is to provide a device which will enable the phlebotomist to effect removal of a used needle from a venipuncturing instrument without risk of becoming pricked by the needle and without his manually contacting the needle in effecting its removal.

A further object of the invention is to provide a device into which the needle end of a conventional venipuncturing instrument may be entered and held so as to allow the body of the instrument to be threadly disconnected from the needle and to allow the disconnected needle to drop through the device into a disposable container below.

A more particular object of the invention is to provide a device into which the unsheathed needle of a venipuncturing instrument of the evacuated tube type may be inserted and cammed against movement so as to enable the user to apply a twisting force to the barrel of the instrument to effect unthreading and separation of the barrel from the needle, and which device includes a disposable container at its bottom into which the needle when disconnected from the instrument will drop upon release of its cammed condition.

An advantageous feature of the invention is a cam element in the device which is pivotable under load of a spring to obtain an interlocked condition with a splined portion of an unsheathed needle of a venipuncturing instrument inserted into a passage of the device, whereby the body of the instrument may be unthreaded from the needle and the disconnected needle will upon subsequent manual pivoting of the cam element out of the interlocked condition against the spring load drop out of the passage into a disposable container.

Another desirable feature of the invention is provided by a spring which is engaged to an arm portion of the cam element and serves to normally bias the cam element so as to provide a holding force of the cam element upon a needle inserted into a passage of the device and thereby enable the body of an associated instrument to be unthreaded from the needle.

While the device of the invention is of particular advantage to the user in effecting for him a safe and protected disengagement and disposal of the unsheathed used needle from a venipuncturing instrument without the user manually touching the needle, the device may also be used for removing and disposing of the sheath from the needle preparatory to use of the instrument.

The invention further lies in its particular structure and in the arrangement of its components as well as in their mode of cooperation with one another to effect the objectives and various advantages intended for it.

BRIEF SUMMARY OF THE INVENTION

The subject of the invention is a device which is particularly suited for use in effecting the removal of the unsheathed used needle from a venipuncturing instrument of the evacuated tube type without danger of the user becoming pricked and possibly infected by the needle. The device includes a disposable container upon which is removably engaged an upper member. The upper member has a vertical passage through it which opens into the container. The needle end of the instrument is adapted to be inserted into the passage, and a manipulative cam in the device is actuable to engage and hold the needle against movement. While the needle is so held, the body of the instrument may be unthreaded from the needle; and the disconnected needle will upon release of its cammed condition drop into the disposable container below. The cam, when actuated, is adapted to interlock with a splined portion of the cylindricle needle, whereby the needle becomes securely restrained against relative movement when the body of the instrument is turned to unthread it from the needle. A spring element is associated with the cam so as to bias the cam to its holding position. Other features and aspects of the invention will become increasingly apparent as this specification unfolds in further detail.

BRIEF DESCRIPTION OF THE DRAWING

In the accompanying drawing:

FIG. 1 is an exploded view of a conventional venipuncturing instrument of the evacuated tube type for which the present invention is particularly suited in effecting removal and disposal of an unsheathed used needle from the instrument;

FIG. 2 is an elevational view partly in section of a device embodying the invention and showing a spring loaded cam of the device in a normal position projecting into a vertical passage of the device;

FIG. 3 is an elevational view of the upper portion of the device and showing the spring loaded cam manipulated to a condition clear of the passage;

FIG. 4 is an elevational view of the upper portion of the device and showing the needle of the instrument inserted into the passage and showing the spring loaded cam engaging the splined portion of the needle; and FIG. 5 is an enlarged fragmentary section of line 5-5 of FIG. 4 and showing the cam in its interlocked engagement with the splined portion of the needle.

DETAILED DESCRIPTION OF THE INVENTION

The invention will now be described with reference to the accompanying drawing and in such concise manner as to enable persons having ordinary skill in the art to make and use the same.

The device embodying the invention includes a lower member or container 1, atop which is removably mounted an upper member 2. The upper member is structured to enable the user to readily effect removal and disposal into the container of the needle member from a conventional venipuncturing instrument of the evacuated tube type, and to do so without manually contacting the needle and without risk of being pricked by the needle.

A conventional venipuncturing instrument of the evacuated tube type is illustrated in FIG. 1. In substance, it includes a rubber stoppered evacuated tube 3, an open-ended supporting body or barrel 4, a double-ended needle 5, and a sheath 6 for covering the needle until the needle is to be used. Intermediately of the ends of the needle is a hub 7, a rear portion 8 of which is threaded and a forward portion 9 of which is straight splined, there being four splines here equally spaced about its periphery.

When the several components of the instrument are assembled together, a rear section 10 of the needle will be disposed in a front end of the barrel with the threaded portion of the hub screwed into complementary threads 11 of a reduced diameter extension 12 of the barrel; and the forward section 13 of the needle together with the splined portion of the hub will both project from the front end of the barrel and will normally be covered by the protective sheath. The sheath will have a splined engagement with the splined portion of the hub. It is apparent that the sheath may be removed by manually pulling it away from the hub; and the needle may be disconnected from the barrel by unscrewing the barrel off the threaded portion of the hub of the needle while holding the projecting end section 13 of the needle against movement.

In making use of the instrument for drawing blood, after the sheath 6 has been removed from the needle, the rubber stoppered evacuated tube 3 with its stoppered end foremost is slidably inserted into the open rear end of the barrel. Then, as the projecting end 13 of the needle is being injected into a patient's vein, the rubber stoppered end of the tube is punctured as the tube is moved against the rear section 10 of the needle. The vacuum in the tube then functions to draw blood from the patient's vein through the hollow needle into the tube. The tube is then withdrawn from the barrel and sent to the laboratory for testing its contents. And, the needle is then disconnected from the barrel to allow the barrel to be reused. As a precautionary measure for safely guarding the phlebotomist from becoming pricked when disconnecting a possibly contaminated used needle from the instrument, the device of the present invention is employed.

The container member 1 of the device is preferably formed of material that is not readily breakable, such as plastic, and it preferably has a broad base 14. The broad base provides the container with a desirable degree of stability whereby it is not readily subject to being tipped over and spilling its contents. The container has a top wall 15 provided at its center with a raised neck 16 through which a passage 17 opens into the container.

The upper member 2 of the device is also preferably formed of plastic material. It is removably mounted upon the container. It has an enlarged annular recess 18 in its bottom end threadedly engaged, as at 19, with complementary threads about the neck of the container. Coaxial with the recess 18 is a relatively narrower annular passage 21 extending vertically through the upper member.

The upper member has a top wall 22 which is preferably level. However, it may be slightly concaved. Passage 21 opens through the center of the top wall; and it is adapted to have the used needle end of a venipuncturing instrument inserted therein for removal of the needle from the instrument. Camming means is provided for restraining the needle against movement in the passage so as to enable the barrel 4 of the instrument to be unscrewed and disconnected from the needle. To this end, a vertical slot 23 opens through a side wall of the upper member into passage 21. Pivoted between the opposed walls of the slot on a pin 24 is a cam 25. The cam has an externally extending arm 26 whereby the cam may be manually pivoted to carry an inner end 27 of the cam into or out of restraining engagement with a needle inserted into the passage 21. This passage, while being of narrow diameter, is adequate to receive with some clearance unsheathed needles as well as sheathed needles of conventional venipuncturing instruments.

The cam is designed to effect a spring pressed interlocking engagement of the cam with the splined portion 9 of the needle so as to restrain the needle against relative turning and thereby enable the barrel of the instrument to be unscrewed from the needle. To this end, a closely coiled spring 28 is engaged at one end to an end area of the cam arm and is anchored at its other end 29 to the body of the upper member. The cam is tensioned by the spring in such manner that it obtains a normal pivoted position in which its body extends into the passage 21 with its front end 27 in close proximity to the opposed wall of the passage, as appears in FIG. 2. The cam may be manually pivoted clockwise from this position against the bias of the spring to a position, as appears in FIG. 3, in which the body of the cam is clear of the passage. While the cam is being manually held in the FIG. 3 position, the needle 13, together with its splined portion 9 and the reduced diameter extension 12 of the barrel of the instrument, may be inserted down into the passage 21 until an enlarged bottom shoulder 31 of the barrel seats upon the top wall of the upper member 2, as appears in FIG. 4.

Following insertion of the needle into the passage, manual release of the cam will allow the cam under the bias of spring 28 to pivot into the passage. The spring loaded cam will press its inner end 27 against the splined portion of the needle and abut the splined portion against the wall of the passage. In this condition, the inner end of the cam may obtain a position abutting the periphery of one of the splines 32 of the splined portion of the needle, or it may be disposed between the splines.

If the cam is disposed between the splines, a side face of one of the splines will abut a slightly angled complementary corner 33 of the cam, whereby the cam and needle will be interlocked against relative rotation of the needle. If the cam, when manually released obtains a condition with its inner end abutting the periphery of one of the splines, then a slight clockwise manipulation of the barrel of the instrument will cause the abutting spline to ride over the end surface of the cam and allow the front end of the cam under the bias of the spring to enter a space between the overridden spline and the spline ahead to obtain the interlocked condition of the cam and the splined portion of the needle, as appears in FIG. 5.

In making use of the device embodying the invention, after the covering sheath has been removed from the needle and the instrument has been used in drawing blood from a patient, the cam is manually pivoted from its normal position against the bias of its spring to clear the passage 21, as appears in FIG. 3, and is so held. The unsheathed used needle is then entered down into the passage 21 until the bottom shoulder 31 of the barrel of the instrument seats upon the top wall 22 of the upper member 2. The cam element is than manually released to effect the interlocked condition of the front end of the cam with the splined portion of the needle, whereby the needle is restrained against rotation relative to the cam. While the needle is so restrained, manual turning of the barrel of the instrument counter-clockwise will effect unscrewing of the barrel from the needle. The barrel will then be lifted away. The cam will then be manually pivoted against the load of its spring out of its interlocked condition, and the unrestrained disconnected needle will then drop through the passage 21 into the container 1 below.

The container is of a size suitable to hold a multiple number of disconnected needles; and when the transparent container is observed to be filled with needles to a level indicated by a line marking 34 on its face, the user will unscrew the container from the upper member 2. He will then close the neck of the container with a screw cap and dispose of it.

While the device will normally be used in effecting the removal of used needles from venipuncturing instruments, it may also be used to remove the sheath from a needle preparatory to use of the instrument in drawing blood.

While an embodiment of the invention has been illustrated and described in detail, it is to be expressly understood that the invention is not limited thereto. Various changes in form, design or arrangement may be made in its components without departing from the spirit and scope of the invention. It is our intent, therefore, to claim the invention not only as shown and described, but also in all such forms and modifications or equivalents thereof as might be construed to be within the spirit of the invention when considered in the light of the specification, the drawing and the appended claims.

What is claimed is:

1. A device for removing from a syringe a used needle which has been screwed into the syringe and which needle has a straight splined portion disposed externally of the syringe, the device comprising: an upper member for effecting removal of the needle, the upper member being removably engaged over the open top of a disposable container lower member, into which container the needle may drop when removed, wherein the upper member has a narrow vertically extending elongated body provided with an open-ended vertical passage through it communicating with the open top end of the disposable container, a cam lever pivotably mounted between opposed vertical side walls of a vertically extending slot that opens through a side of the body into the passage, the cam lever having a cam end surface that is movable into the passage to restrict the passage accordingly as the cam lever is pivoted in one direction and is movable clear of the passage accordingly as the cam lever is pivoted in an opposite direction, spring means biasing the cam lever in the direction in which its cam surface restricts the passage, and the cam lever being manually actuable in the opposite direction against the bias of the spring means to move its cam surface clear of the passage, and wherein the passage is adapted upon movement of the cam surface clear of the passage to have a needle of a syringe with the splined portion of the needle entered into the passage, and the cam lever is adapted upon being manually released to enter under bias of the spring means its cam surface into the passage into engagement with the splined portion so as to restrain the position of the entered needle to allow the syringe to be unscrewed from the needle, and wherein the cam lever is adapted upon its cam surface being subsequently manually pivoted clear of the passage and of the needle to allow the needle from which the syringe has been unscrewed to drop down the passage into the disposable container below.

2. A device including an upper member for holding the used needle of a syringe so as to allow the syringe to be unscrewed from the needle and for releasing the needle after unscrewing of the syringe so as to allow the needle to drop into a lower container member of the device, wherein the upper member has relative to the container a relatively narrow vertically extending elongated body, the body being provided with an open-ended vertical passage through it communicating with an open top of the container, a cam lever povotable between opposed vertical side walls of a vertically extending slot that opens through a side of the body into the passage, the cam lever having a cam end surface that is movable into the passage to restrict the passage accordingly as the cam lever is pivoted in a predetermined vertical direction and is movable clear of the passage accordingly as the cam lever is pivoted in an opposite direction, spring means biasing the cam lever in the direction in which its cam surface restricts the passage, and the cam lever being manually actuable in the opposite direction against the bias of the spring means to move its cam surface clear of the passage, wherein the cam surface is adapted upon being moved into the passage to hold a used 3. A device as in claim 2, wherein the elongated body is threadedly engaged at a bottom end thereof with the disposable container whereby it may be unscrewed from the container.

4. A device as in claim 3, wherein the disposable container is of a plastic material enabling a visual inspection as to the contents of the container.

5. A device for removing from a syringe a used needle which has on a rear area thereof a threaded portion screwed into the syringe and which needle has adjacent to the threaded portion and disposed externally of the syringe a straight splined portion, the device comprising: an elongated body removably mountable atop a container, an open-ended vertical passage extending axially through the body and alignable with an opening in a container upon which the body may be mounted, a cam element pivotably mounted between opposed vertical walls of a vertically extending slot that opens through a side of the body into the vertical passage, spring means biasing the cam element about its pivot into the passage and the cam element being adapted to being manually pivoted against the bias of the spring means out of the passage, the passage being adapted when the cam element has been pivoted out of the passage to have the used needle and its splined portion entered therein, and the cam element adapted upon being pivoted into the passage to engage under pressure of the spring means the splined portion so as to restrain the needle against rotation as the syringe is unscrewed from the needle, and the cam element adapted upon being manually pivoted clear of the passage to allow the needle from which the syringe has been unscrewed to drop out of the passage into a container upon which the device may have been mounted.

* * * * *